(12) United States Patent
Sekiguchi

(10) Patent No.: US 7,333,636 B2
(45) Date of Patent: Feb. 19, 2008

(54) FUNDUSCOPIC IMAGE PROCESSING UNIT AND METHOD

(75) Inventor: Kyoji Sekiguchi, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 509 days.

(21) Appl. No.: 10/970,337

(22) Filed: Oct. 21, 2004

(65) Prior Publication Data
US 2005/0089207 A1 Apr. 28, 2005

(30) Foreign Application Priority Data
Oct. 24, 2003 (JP) .............................. 2003-364399

(51) Int. Cl.
*G06K 9/00* (2006.01)
(52) U.S. Cl. .................. 382/117; 348/78; 351/206; 351/207; 351/208
(58) Field of Classification Search ........... 382/117, 382/282, 283, 128, 351, 171, 168–172; 348/77–78; 351/206, 207, 208
See application file for complete search history.

(56) References Cited

U.S. PATENT DOCUMENTS 4,365,872 A * 12/1982 Nunokawa .................. 351/208
4,715,703 A * 12/1987 Cornsweet et al. ......... 351/205
5,455,644 A * 10/1995 Yazawa et al. ............. 351/206
5,710,842 A * 1/1998 Lee ........................... 382/283
2002/0131017 A1* 9/2002 Kishida et al. ............. 351/206

FOREIGN PATENT DOCUMENTS

| JP | A 3-193026 | 8/1991 |
| JP | 09-206278 | 8/1997 |
| JP | 09206278 A * | 8/1997 |
| JP | A 9-206278 | 8/1997 |

* cited by examiner

*Primary Examiner*—Bhavesh M Mehta
*Assistant Examiner*—John B Strege
(74) *Attorney, Agent, or Firm*—Morgan & Finnegan LLP

(57) ABSTRACT

To determine the presence or absence of an aperture mask in a funduscopic image output by a fundus camera, and to combine the funduscopic image with an aperture mask image formed in an aperture mask-forming section so as to correspond to a determination result. When an aperture mask determination section 34 determines the absence of the aperture mask image in the funduscopic image and the necessity of the addition, the aperture mask-forming section 35 forms a necessary mask, and an aperture mask combine section 36 combines the funduscopic image with the aperture mask image.

9 Claims, 8 Drawing Sheets

FUNDUSCOPIC IMAGE PROCESSING UNIT AND METHOD

BACKGROUND OF THE INVENTION

1. Field of the Invention

The present invention relates to a technology suitable for funduscopic image processing for displaying a funduscopic image output from a fundus camera used in departments of ophthalmology and internal medicine.

2. Related Background Art

The present invention relates to a funduscopic image processing unit for correctly displaying a funduscopic image output from a fundus camera used in departments of ophthalmology and internal medicine.

FIG. 7 shows a periphery of a photographic camera of a fundus camera having means for photographing an aperture mask. Right in front of an imaging face of the photographic camera 1 for static images, an aperture mask plate 3 having a circular opening 2 provided in the center and a shading part around it, is arranged as shown in FIG. 8.

A funduscopic image is caught in the center of a photographic light flux from a photographic optical system of a fundus camera, but a flare is mixed with the funduscopic image in the perimeter, and undesired reflection and the like are mixed with the funduscopic image outside the perimeter, so that the opening 2 of an effective region for diagnosis, is preferably clarified by an aperture mask plate 3.

In this case, the aperture mask plate 3 has to be arranged in such a vicinity of the imaging face of a photographic camera 1 as not to blur a mask border. However, if various filters and a changeover mirror 4 are arranged right in front of an imaging face, it is rather difficult to further install the aperture mask plate 3 there.

Particularly, in the case of using a three-plate camera having three image sensors behind a color-splitting prism such as a 3P prism, the camera has to optically reimage an aperture mask plate 3 and a funduscopic image in order to photograph an image of the aperture mask plate 3, as a result, needs to make an optical path longer, an optical system complicated and the number of mechanisms increased, and causes problems of an increase of the cost and the like.

In recent years, a fundus camera is proposed which in order to reduce the cost, miniaturizes the unit and reduces the weight, simplifies the optical system and mechanisms, eliminates the above described aperture mask plate 3, and makes the whole image of a photographically effective area of a photographic optical system produced on the imaging face. By such means, the photographic system eliminates an optical system for reimaging, thereby miniaturizes a fundus camera itself, and reduces the cost.

As described above, there are various types in funduscopic images photographed by a conventional fundus camera, as shown in FIGS. 9A to 9D. FIGS. 9A and 9B show funduscopic images with the use of an aperture mask plate 3, and FIGS. 9C and 9D show funduscopic images without the use of an aperture mask plate 3. FIG. 9A shows a funduscopic image of an ocular fundus, which shows an orbicular funduscopic image Er', is photographed at the same view angles both in vertical and horizontal directions, and catches an aperture mask image M in the perimeter. In FIG. 9B, the photographic optical system effectively arranges both of an effective optical path and an imaging face therein, and catches a funduscopic image Er' as an oval and oblong shape in a horizontal direction and an aperture mask image M around it.

In FIG. 9C, the photographic optical system arranges all imaging faces inside a photographing light flux, and catches a funduscopic image Er' on the whole image plane. FIG. 9D shows a funduscopic image Er' which schematically shows a flare, and in which flares F1, F2 and F3 are sequentially caught outside an effective funduscopic image Er'. The flare F1 is an area in which a funduscopic image is photographed together with a flare. In the flare F2, a funduscopic image, an image in a fundus camera and a flare are shown. In the flare F3, a blurred image in a fundus camera is darkly shown. In Japanese Patent Application Laid-Open No. H09-206278, it is disclosed to electrically and electronically add an aperture mask image to a funduscopic image photographed by the above fundus camera.

There is no problem in using a fundus camera integrated with means for mask processing, as described above. However, in the case of using a fundus camera in fundus photography for health examination, diabetic retinopathy and a diagnosis of glaucoma, a diagnosis based on a photographed funduscopic image is generally carried out in a different place from that for the fundus photography. Particularly, a small, light weight and inexpensive product is demanded for the fundus camera, which causes a problem that a fundus camera hardly integrates means for mask processing in its inside.

In addition, because various old and new fundus cameras described above are installed in a hospital or a physical examination organization which carries out fundus photography for such examinations, if a funduscopic image as shown in FIG. 9D is mixed, it may cause a wrong diagnosis because of the image which does not define an effective range of an ocular fundus. Furthermore, because it is hard to observe and interpret the image having no boundary, such images cause the problem of imposing a heavier load of easily being tired onto an image diagnostician.

SUMMARY OF THE INVENTION

The present invention has been accomplished in view of the above problems, and is directed to providing a suitable technology for funduscopic image processing for displaying a funduscopic image which is output from a fundus camera used in departments of ophthalmology or internal medicine.

In order to achieve the above object, for example, a funduscopic image processing unit of the present invention comprises the following arrangement.

That is, a funduscopic image processing unit comprises: image-inputting means for inputting funduscopic image data, and image-processing means for carrying out a predetermined image processing to the funduscopic image data, wherein the predetermined image processing is carried out on the basis of a determination result of aperture mask determination means for determining the presence or absence of an aperture mask image in the funduscopic image data.

In order to achieve the above object, for example, a funduscopic image processing method of the present invention comprises the following arrangement.

That is, a funduscopic image processing method comprises: an image-inputting step for inputting funduscopic image data, and image-processing step for carrying out a predetermined image processing to the funduscopic image data, wherein the predetermined image processing is carried out on the basis of a determination result in an aperture mask determination step for determining the presence or absence of an aperture mask image in the funduscopic image data.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Figure 1:
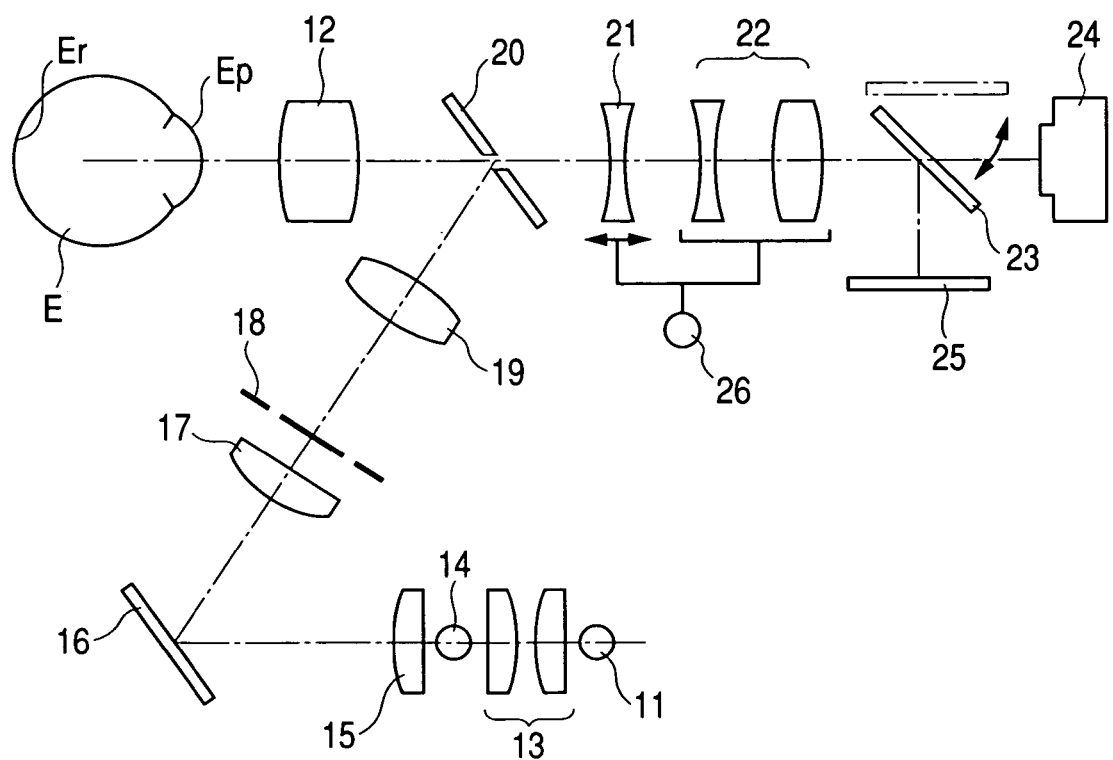
FIG. 1 is a block diagram of a fundus camera according to the embodiment 1.

Preferred embodiments of the present invention will now be described in detail in accordance with the accompanying drawings.

The present invention will be described in detail with reference to embodiments shown in the drawings.

Embodiment 1

FIG. 1 shows a block diagram of a fundus camera without means for photographing an aperture mask. The fundus camera has, on an optical path to an object lens 12 from an alignment light source 11 for observation such as a lamp, a condensing lens 13, a light source 14 for photographing a static image such as a stroboscope, a condensing lens 15, a mirror 16, a lens 17, an aperture 18 having a ring-shaped opening, a relay lens 19, and an apertured mirror 20 having an aperture in a central part, sequentially disposed.

A fundus camera also has, on an optical path at the rear of an opening mirror 20, a movable focus lens 21, a taking lens 22 having a scaling function, a changeover mirror 23 and a camera 24 for photographing a high-definition static image, sequentially arranged therein; has a high-sensitivity camera 25 for observing a moving image arranged in the reflecting direction of the changeover mirror 23; and has a focus knob 26 installed to drive the focus lens 21 and the taking lens 22.

In an observation and alignment step, a flux of light emitted from a light source 11 for alignment for observation, passes through a condensing lens 13, a light source 14 for photographing a static image and a condensing lens 15, then is reflected upward by a mirror 16, then passes through a lens 17, a ring-shaped opening of an aperture 18 and a relay lens 19, then is reflected toward left by an opening mirror 20, and passes through an objective lens 12 to illuminate an ocular fundus Er through a pupil Ep of an eye to be examined E. A reflected light from thus illuminated ocular fundus Er passes through the pupil Ep, the objective lens 12, a focus lens 21 and a taking lens 22, then is reflected downward by a changeover mirror 23, and produces an image as a funduscopic image Er', on the imaging face of a camera 25 for observing a moving image.

A photographer confirms a photographing portion, alignment and a focal condition while observing a funduscopic image Er' through a monitor which is not be shown, and when the image is out of focus, a photographer adjusts the focus by moving a focus lens 21 to an optical axis direction through an operation for a focus knob 26.

After completing a photographing preparation, an examiner pushes a photographic switch which is not shown, then a changeover mirror 23 retreats to the outside of an optical path, and a light is emitted from a light source 14 for photographing a static image. The flux of light passes through a lens 15 and then an optical path similar to the flux of the light emitted from a light source 11 for observation and alignment, and illuminates an ocular fundus Er. The reflected light from the ocular fundus Er passes through a pupil Ep, then an objective lens 12, an opening mirror 20, a focus lens 21 and a taking lens 22, and forms an image as a funduscopic image Er' on the imaging face of a camera 24 for photographing the static image.

An image formed on the imaging face is only a central effective part without a flare of a photographed funduscopic image Er'. The photographed image is converted to electric signals in a camera 24 for photographing a static image, and then is displayed on a monitor. In addition, the funduscopic image Er' is stored in a storage unit which is not shown, and is transferred via a communication line and a network.

Figure 2:
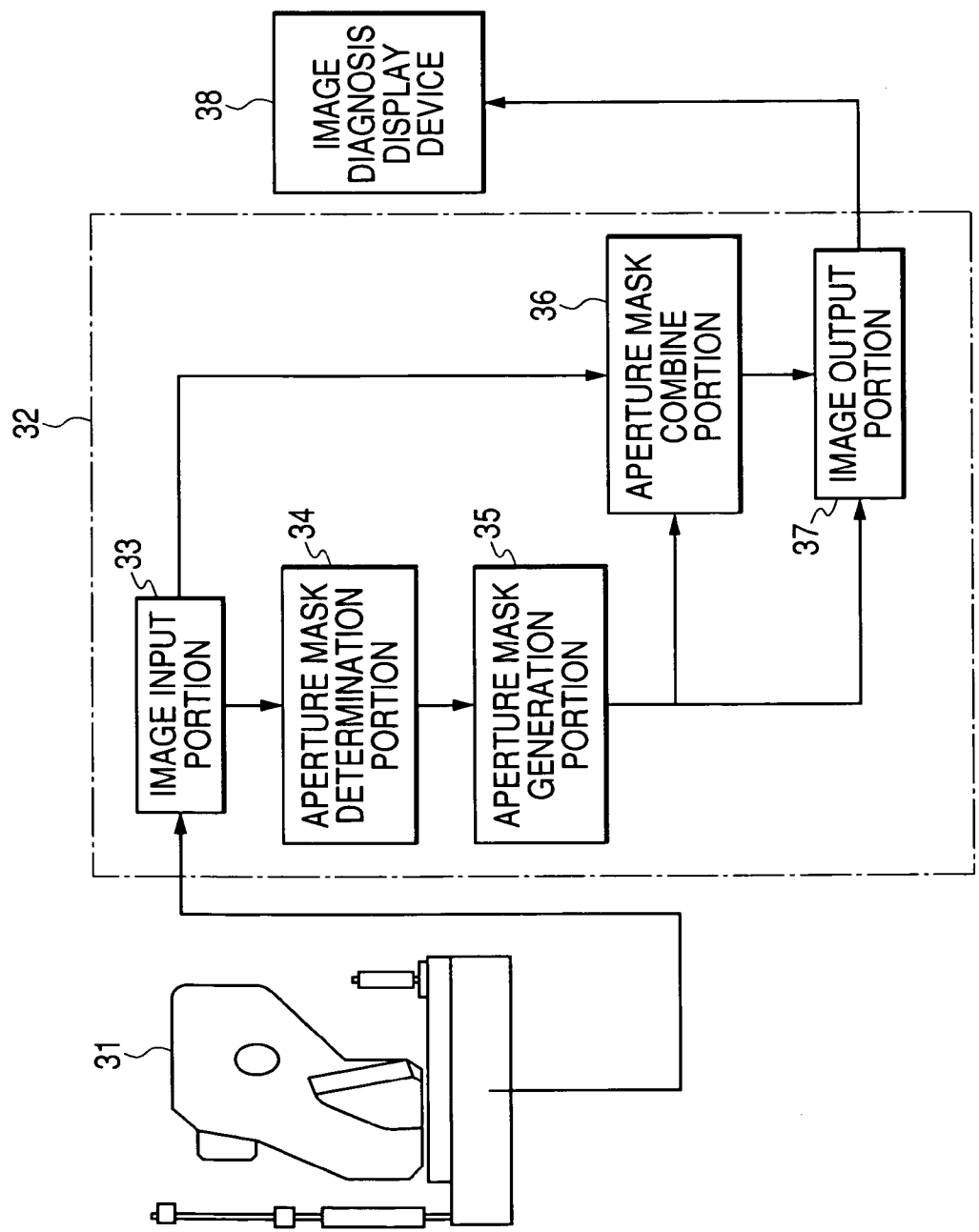
FIG. 2 is a block diagram in an image processing unit according to the embodiment 1.

FIG. 2 shows a block diagram in an image processing unit. The output of a fundus camera 31 for photographing an image without an aperture mask is connected to a funduscopic image processing unit 32. The signals of a funduscopic image Er' output from a fundus camera 31 is connected to an image-inputting section 33 in the funduscopic image processing unit 32, and the output of an image-inputting section 33 is sequentially connected to an aperture mask-forming section 35 through an aperture mask determination section 34, and then to an image-outputting section 37 through an aperture mask combine section 36. Furthermore, the output of an aperture mask-forming section 35 is connected to the aperture mask combine section 36 and the image-outputting section 37, and the image-outputting section 37 is connected to an external image diagnosis display device 38.

When a fundus camera 31 is used for fundus photography, a photographed funduscopic image is sent to an image-inputting section 33 in a funduscopic image processing unit 32, and is developed in a memory for image processing, which is not shown, and there initialized so that it can be treated in an aperture mask determination section 34 and an aperture mask combine section 36. In the aperture mask determination section 34, it is determined whether an aperture mask image M has to be added to a funduscopic image Er', or not, by a method described below. When it is determined that a funduscopic image Er' has no aperture mask image M and needs the addition thereof, a necessary mask is formed in an aperture mask-forming section 35, an aperture mask image M combined with the formed mask is produced in the aperture mask combine section 36, the format is converted in the image-outputting section 37, and the combined image is output to an image diagnosis display device 38.

In addition, the aperture mask image formed in an aperture mask-forming section 35 can be independently output to an image-outputting section 37, and when an image diagnosis display device 38 has an overlay function, a funduscopic image and an aperture mask image can be separately input, overlaid and displayed.

Embodiment 2

Figure 3:
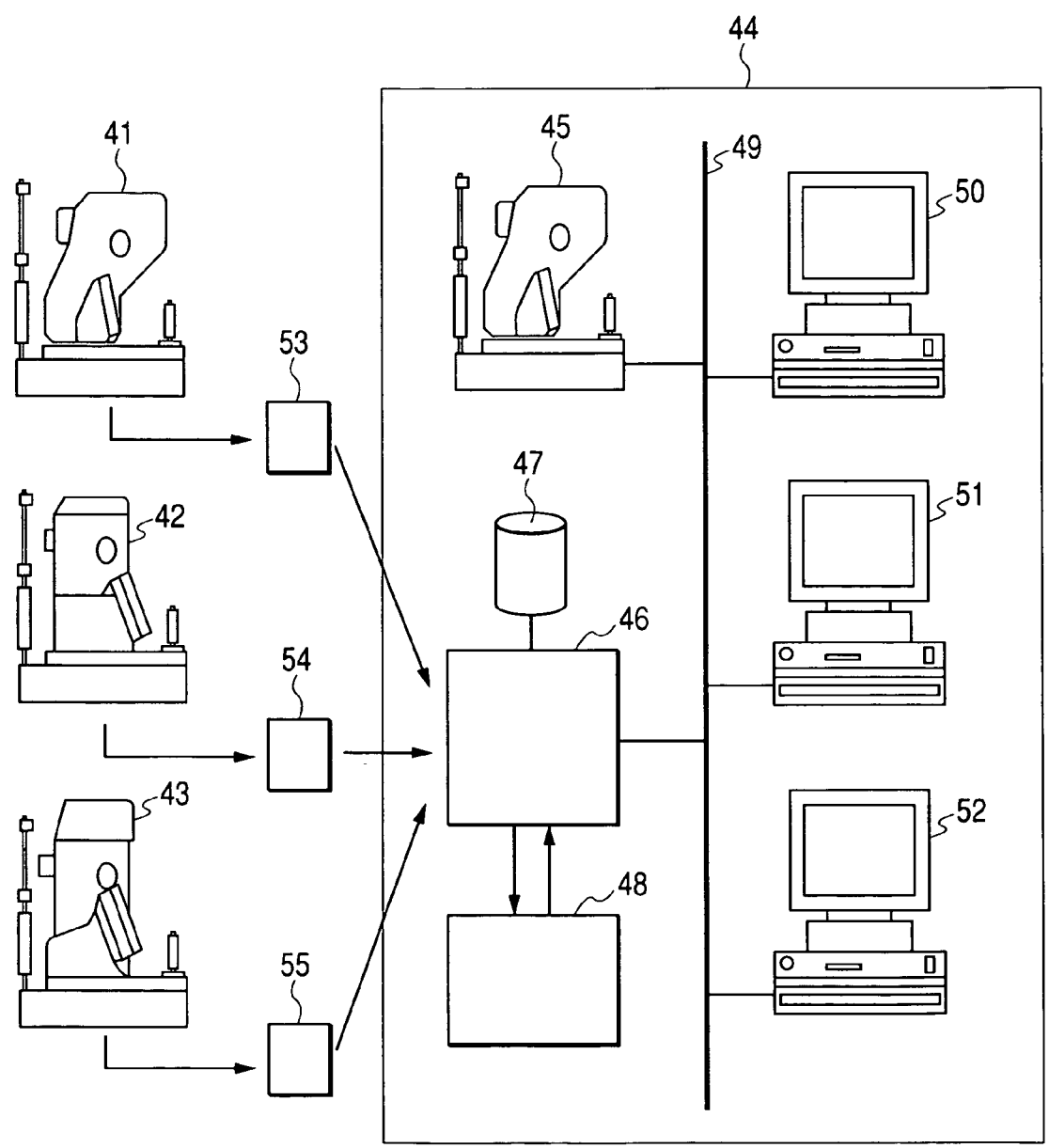
FIG. 3 is a block diagram in an image processing unit according to the embodiment 2.

FIG. 3 shows a block diagram in the case of photographing funduscopic images with several different fundus cameras in the embodiment 2. Outside a hospital having an image processing unit, there are a fundus camera 41 for forming a funduscopic image having no aperture mask image, a fundus camera 42 forming an image catching an aperture mask, and a fundus camera 43 of which the whole image is a funduscopic image. In a hospital 44, there installed are another fundus camera 45, an image server 46 for accumulating image data and an image-storing section 47, and to a server 46, a funduscopic image processing unit 48 is connected. To the image server 46, the fundus camera 45 and image diagnosis display devices 50, 51 and 52 are connected through a network 49. The funduscopic images photographed with the fundus cameras 41, 42 and 43 outside the hospital 44 are input in the image server 46 in the hospital 44 and is kept in the image-storing section 47 through removable storage media 53, 54 and 55.

The funduscopic images photographed with fundus cameras 41, 42 and 43 are photographed into various forms as shown in FIGS. 9A to 9D. When a request asking to display a funduscopic image Er' is output to an image server 46, for instance, from a funduscopic image processing unit 32 shown in FIG. 2, the image server 46 searches the funduscopic image Er' in an image-storing section 47 and sends it to a funduscopic image processing unit 48. The funduscopic image processing unit 48 determines whether the aperture mask image as described in FIG. 2 exists in the funduscopic image, or not, produces an image combined with an aperture mask in accordance with the result, and returns a resultant image to the image server 46. To images requiring an aperture mask image M in order to be displayed by image diagnosis display devices 50, 51 and 52 via a network 49, the processing unit 48 can appropriately add them the aperture mask image so as to be displayed together with it.

Embodiment 3

Figure 4:
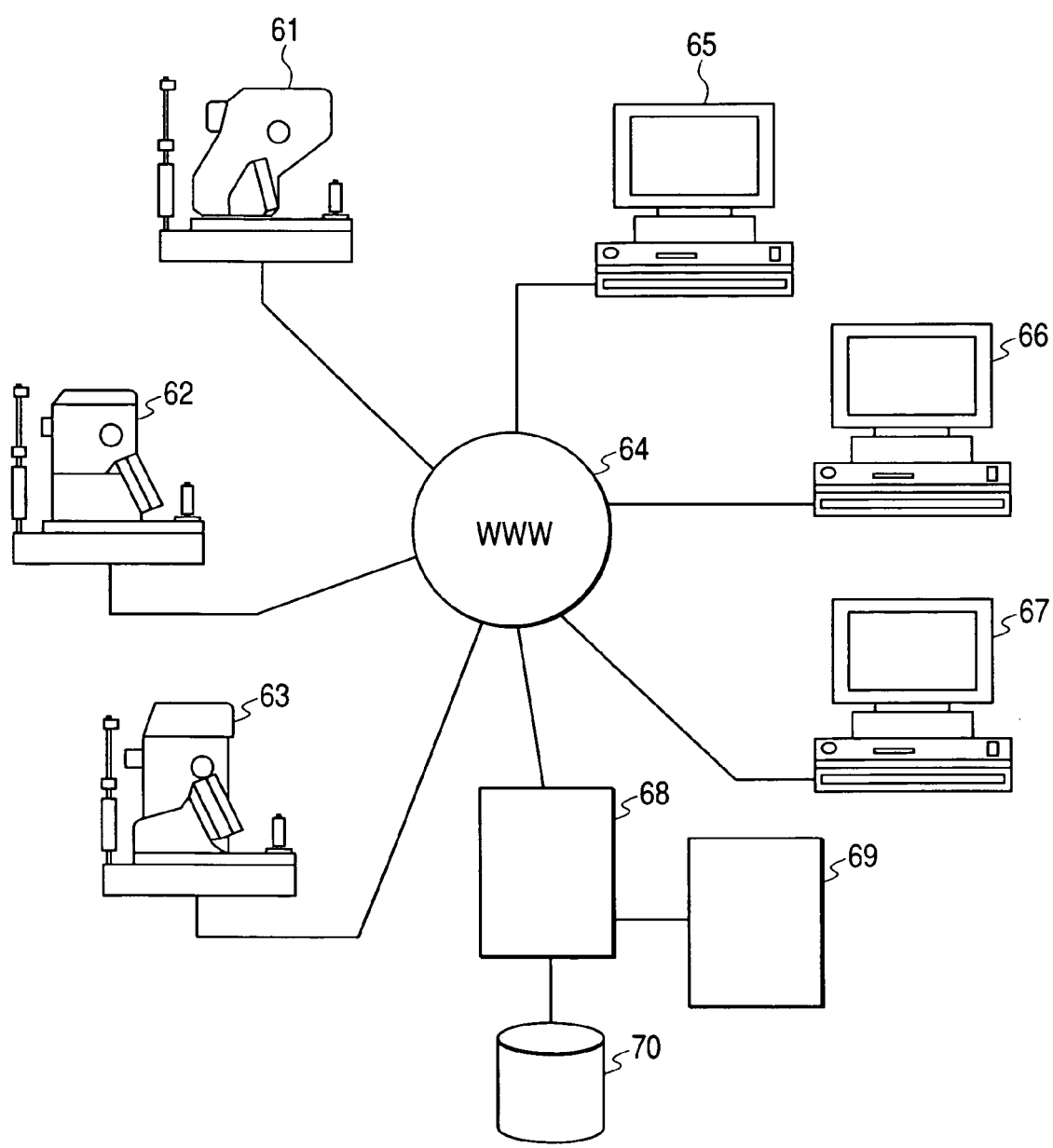
FIG. 4 is a block diagram in an image processing unit according to the embodiment 3.

FIG. 4 shows a block diagram of an image processing unit in the case of connecting several different fundus cameras in the embodiment 3 via the Internet. The outputs of fundus cameras 61, 62 and 63 are connected to diagnostic-imaging display units 65, 66 and 67 of a terminal and to an image server 68, through an Internet network 64, and further to an image server 68, a funduscopic image processing unit 69 and an image-storing section 70 are connected.

In the present embodiment, photographed images with fundus cameras 61, 62 and 63 for outputting various funduscopic images as in the case of the embodiment 2, are temporarily sent to an image server 68 via an Internet network 64, and are memorized and kept in an image-storing section 70. In addition, when receiving requests asking for sending images from image diagnosis display devices 65, 66 and 67 in distant various places and countries, the image server 68 searches funduscopic images Er' matching to the requests, sends them to a funduscopic image processing unit 69, receives the processing result, and sends the images to requesters. In the above case as well, the aperture mask processing described above is carried out, and the images having an aperture mask image M correctly added, are sent to the terminals of the image requesters.

Figure 5:
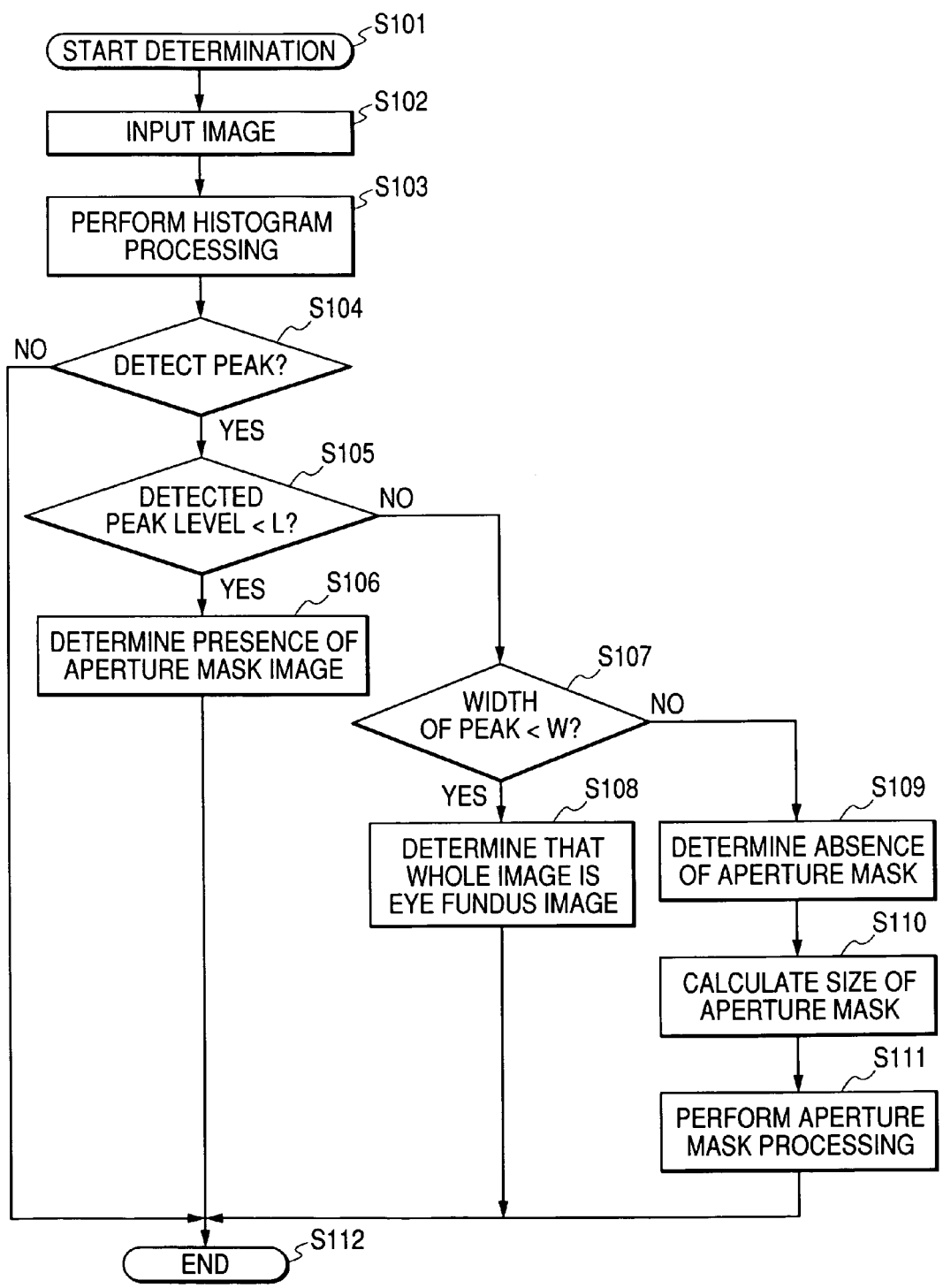
FIG. 5 is a flow chart of a method for detecting an aperture mask.

FIG. 5 shows a flow chart of a determination method for determining the presence or absence of an aperture mask image, which has been carried out in each embodiment. At first, the determination starts in a step S101, and an image to be detected is input to a memory in a step S102. Subsequently, image processing means carries out a histogram processing in a step S103. In the case of a color image, the histogram processing is carried out after being converted to brightness information.

Figure 6A:
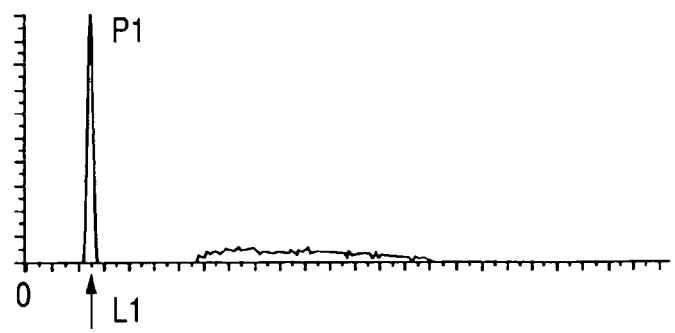
FIGS. 6A, 6B, 6C and 6D are graphical views of histogram treatment.

The result of histogram processing is output as shown in FIG. 6A, for instance. The horizontal axis shows a pixel value. In the case of an 8-bit image, an origin point is 0 and the right end is 255. In the case of a 10-bit image, the right end is 1023. The right end shows the highest brightness level. The vertical axis shows a frequency count, and shows that the number of pixels having a certain level increases with the height. In FIGS. 6A to 6D, the peaks of the vertical axis are arranged and normalized, so that the value itself of the vertical axis does not indicate a frequency count.

FIGS. 6A to 6D show the result of histogram processing for each funduscopic image shown in FIGS. 9A to 9D. The horizontal axis shows an image value, which increases toward a right side. In other words, when the image value is brightness, a larger value indicates higher luminosity. The vertical axis indicates the frequency count of pixels having the value of the level. Because each graphical view is normalized so as to match with the maximum value of the peak, the height of the vertical axis can not be compared each other among graphical views.

Figure 6B:
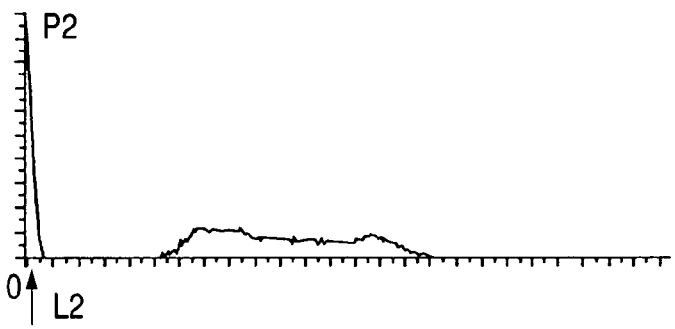
Figure 9A:
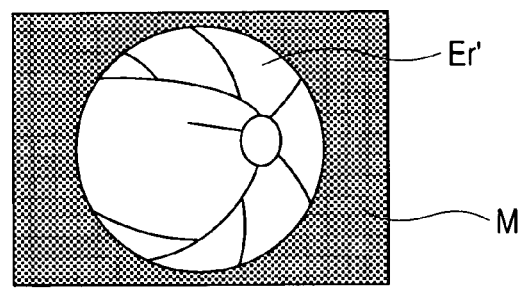
FIGS. 9A, 9B, 9C and 9D are explanatory drawings of a funduscopic image depending on an aperture mask.
Figure 9B:
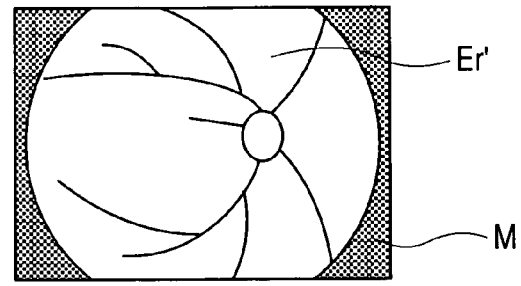
Figure 9C:
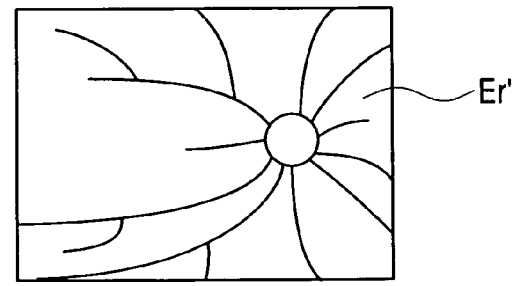
Figure 9D:
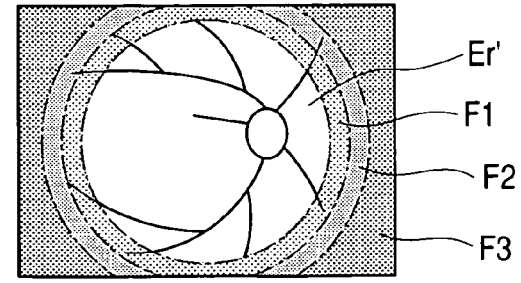

In the image having an aperture mask image M added in the periphery, as shown in FIGS. 9A and 9B, the aperture mask image M has the luminous level of an approximately equal value, and as a result, shows sharp peaks P1 and P2 as shown in FIGS. 6A and 6B.

The level value L1 in FIG. 6A, and the level value L2 in FIG. 6B are the level values L. The difference in the level values L is attributed to the difference in a black level between photographic cameras. As described above, a determination section uses the fact that a funduscopic image Er' having an aperture mask image M has a sharp peak with a small width at the position not larger than a predetermined level value, as a criterion of determination.

Figure 6C:
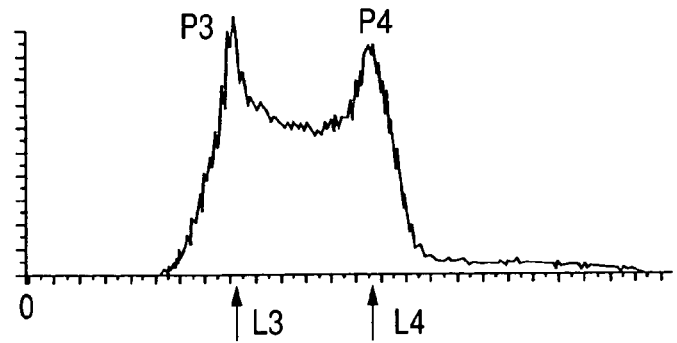
Figure 6D:
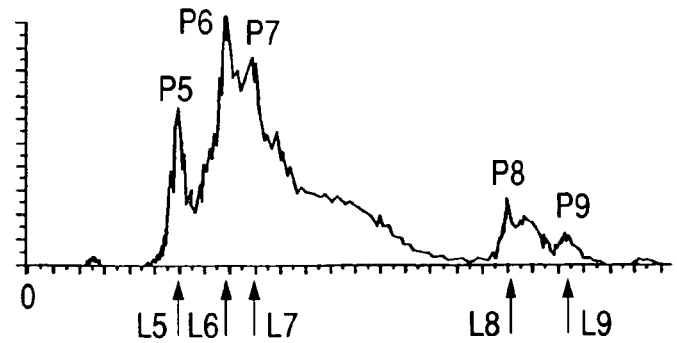
Figure 7:
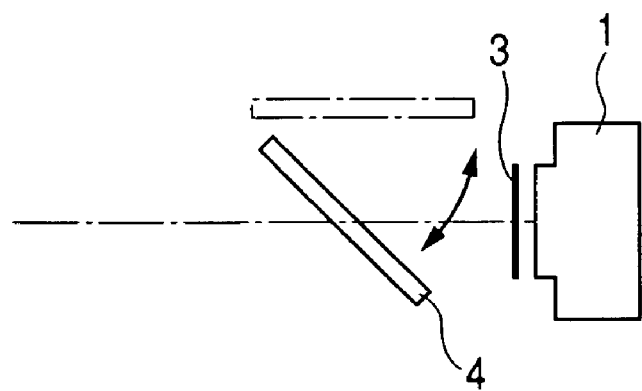
FIG. 7 is a block diagram in a fundus camera provided with an aperture mask plate.
Figure 8:
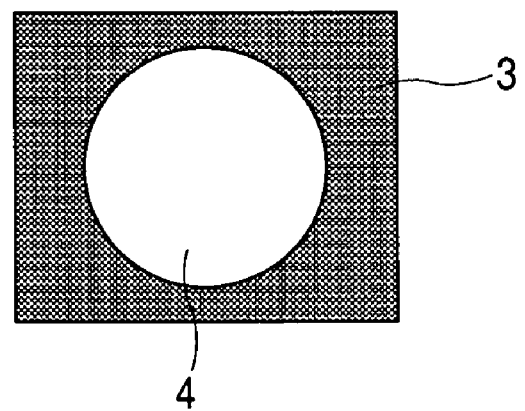
FIG. 8 is a front view of an aperture mask.

FIG. 6C shows a histogram for a funduscopic image displayed in the whole image plane. The histogram contains almost all image values (pixel values) in an intermediate level, and besides has no sharp peak with a small width. In FIG. 6D, because the funduscopic image has a white flare in the periphery, the histogram has a peak in a brighter level than that in an ocular fundus, and because the funduscopic image has a dark image further in the periphery, the histogram has some peaks appearing in the low levels which mean the dark space of a funduscopic image.

After carrying out histogram processing, an aperture mask determination section carries out peak detection processing in a step S104 on the basis of the result, specifically, detects one peak on the basis of an inclination of an ascent, a vertex, an inclination of a descent, a height and a half width, of the peaks. When the determination section has detected the peak, it proceeds to a step S105, and when having detected no such a peak, it proceeds to the determination-finishing step of a step S112 and completes the determination steps.

When having detected a peak, then in a step S105, a determination section determines whether the peak detected in a step S104 is equal to or less than a predetermined value L, or not. Because an aperture mask image M caught in the periphery of a funduscopic image Er' is dark and has a low level, the determination section determines whether the image contains the aperture mask or not from a determination level L. If the level is lower than the determination level L, the determination section determines that there is the aperture mask image, and proceeds to a step S106, and then to the determination-finishing step of a step S112 and completes the determination steps.

When a detected level is determined to be not lower than a determination level L in a step S105, a determination section goes to a step S107. There, the determination section determines the width of the whole image from the result of the peak detection while considering the whole image as a mountain, determines the width of the mountain on the basis of a half value (height) of the obtained lowest peak, and compares the width with a determination value W. If the width of the mountain is less than a determination value W, it means that a level of an image is concentrated in a central part, and in a step S108, the determination section determines that the whole image is a funduscopic image, goes to a step S112 and completes the determination steps. When the width of the mountain is determined to be not less than the detected value W, the determination section goes to a step S109, and in the step S109, determines that there is no aperture mask image M, and then image processing means calculates the size of the aperture mask image M in a step S110.

Calculation is carried out in the following way. On the basis of a pixel level L9 of a brightest peak P9, image processing means seeks and determines a position having a brightness approximately equal to the pixel level L9 centrifugally from the center of the image in at least two directions, considers the distance between the sought position and the center as the radius of an aperture mask image M, and determines the mask size. Subsequently, in a step S111, the image processing means adds the aperture mask image M on the basis of the determined mask size. In the step, the level of the mask in itself is made to be a black level=0. Then, the image processing means goes to a step S112 and finishes the determination steps.

A funduscopic image processing unit according to the present invention correctly determines whether a funduscopic image output from various imaging types of fundus cameras have an aperture mask area or not, determines whether the funduscopic image contains an unnecessary area for interpretation of a funduscopic image or not, and produces a funduscopic image combined with an aperture mask so as to correspond to the area. Accordingly, a diagnostician can safely diagnosis the symptom from the image with little fear of a wrong diagnosis.

In addition, when the places of fundus photography and image diagnosis are distant from each other, a funduscopic image processing unit can put an aperture mask to an image having no aperture mask, and sends it when sending the image, thereby an interpretation doctor does not need a special image processing unit, and can diagnose the symptom with a general-purpose display unit. As described above, the present invention provides a technology suitable for funduscopic image processing for displaying a funduscopic image outputted from a fundus camera used in departments of ophthalmology and internal medicine.

It is needless to say that the object of the present invention is also achieved by supplying a recording medium (or a storage medium) that records a program code of software which realizes the functions of the above described embodiments, to a system or an apparatus, and making the computer (or CPU or MPU) of the system or the apparatus read and carry out the program code stored in the recording medium. In this case, the program code read from the recording medium by itself realizes the functions of the above described embodiments, and the recording medium which records the program code constitutes the present invention.

In addition, it is needless to say that the present invention includes not only the case in which the functions of the above described embodiments are realized by the execution of the program code read by the computer, but also the case in which the functions of the above described embodiments are realized by the processing by an operating system (OS) or the like operating on the computer which carries out one or all of actual treatment on the basis of directions from the program code.

It is also needless to say that the present invention includes the case in which the program code read from the recording medium is written on a functionality expansion card inserted to the computer or a memory installed in a functionality expansion unit connected to the computer, and then a CPU mounted on the functionality expansion card or the functionality expansion unit carries out one or all of the actual processing on the basis of directions of the program code, and the functions of the above described embodiments are realized by the processing.

When the present invention is applied to the above described recording medium, the program code corresponding to the flow chart described above shall be stored in the recording medium.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2003-364399 filed Oct. 24, 2003, which is hereby incorporated by reference herein.

What is claimed is:

1. A funduscopic image processing unit comprising:
    image-inputting means for inputting funduscopic image data, and
    image processing means for carrying out a predetermined image processing to the funduscopic image data,
    wherein the predetermined image processing is carried out on the basis of a determination result of aperture mask determination means for determining the presence or absence of an aperture mask image in the funduscopic image data.

2. The funduscopic image processing unit according to claim 1, wherein the image processing means forms an aperture mask image corresponding to the funduscopic image data on the basis of the result of the aperture mask determination means.

3. The funduscopic image processing unit according to claim 1, wherein the image processing means combines the funduscopic image data with an aperture mask image on the basis of the result of the aperture mask determination means.

4. The funduscopic image processing unit according to claim 1, wherein the aperture mask determination means determines whether the image should have the aperture mask image, need no aperture mask image, or need the aperture mask image, on the basis of the funduscopic image data input by the image-inputting means.

5. The funduscopic image processing unit according to claim 4, the determination for the presence or absence of the aperture mask image is carried out on the basis of the result of histogram processing on the funduscopic image data.

6. The funduscopic image processing unit according to claim 1, wherein the image-processing means calculates an aperture mask size required for the funduscopic image data on the basis of the result of the aperture mask determination means.

7. A funduscopic image processing method comprising:
an image-inputting step for inputting funduscopic image data, and
an image processing step for carrying out a predetermined image processing to the funduscopic image data,
characterized in that the predetermined image processing is carried out on the basis of a determination result of an aperture mask determination step for determining the presence or absence of an aperture mask image in the funduscopic image data.

8. A computer readable medium for executing a funduscopic image processing method by a computer, the method comprising:
receiving a funduscopic image from a camera;
determining the presence or absence of an aperture mask image in the funduscopic image; and
carrying out a predetermined image processing onto the funduscopic image of the basis of a determination results of the aperture mask determination section.

9. A funduscopic image processing unit comprising:
an image-inputting section which is adapted to receive a funduscopic image from image a camera;
an aperture mask determination section which is adapted to determine the presence or absence of an aperture mask image in the funduscopic image; and
an image processing section which is adapted to carry out a predetermined image processing onto the funduscopic image on the basis of a determination result of the aperture mask determination section.

* * * * *